United States Patent [19]

Nadelson

[11] 4,170,705

[45] Oct. 9, 1979

[54] SUBSTITUTED HYDROXY PYRIDONES

[75] Inventor: Jeffrey Nadelson, Denville, N.J.

[73] Assignee: Sandoz, Inc., E. Hanover, N.J.

[21] Appl. No.: 925,197

[22] Filed: Jul. 17, 1978

Related U.S. Application Data

[60] Division of Ser. No. 771,006, Feb. 22, 1977, Pat. No. 4,122,182, which is a continuation-in-part of Ser. No. 693,703, Jun. 7, 1976, abandoned.

[51] Int. Cl.² .............................................. C07D 213/44
[52] U.S. Cl. ..................................... 546/296; 424/263; 546/116; 548/248
[58] Field of Search ................... 260/296 R, 297 C; 424/263; 546/296

[56] References Cited

U.S. PATENT DOCUMENTS

| 4,024,262 | 5/1977 | Nadelson | 260/296 H X |
|---|---|---|---|
| 4,103,013 | 7/1978 | Nadelson | 424/263 |
| 4,120,967 | 10/1978 | Nadelson | 424/263 |
| 4,122,182 | 10/1978 | Nadelson | 546/296 |
| 4,131,679 | 12/1978 | Nadelson | 424/263 |

*Primary Examiner*—John D. Randolph
*Attorney, Agent, or Firm*—Gerald D. Sharkin; Robert S. Honor; Timothy G. Rothwell

[57] ABSTRACT

Substituted hydroxy pyridones, e.g., 3-(α-N-methyliminobenzyl)-4-hydroxy-6-phenyl-1-methyl-2(1H)-pyridone, are prepared by reacting a corresponding substituted hydroxy pyridone carbonyl with an alkyl amine, and are useful as minor tranquilizers, sleep inducers, muscle relaxants, and neuroleptics.

1 Claim, No Drawings

SUBSTITUTED HYDROXY PYRIDONES

This is a division of application Ser. No. 771,006 filed Feb. 22, 1977, now U.S. Pat. No. 4,122,182 granted Oct. 24, 1978, which in turn is a continuation-in-part of Ser. No. 693,703, filed June 7, 1976, now abandoned.

This invention relates to substituted hydroxy pyridones which exhibit minor tranquilizer, sleep inducer, muscle relaxant and neuroleptic activity. In particular, it relates to 3-substituted-4-hydroxy-6-substituted or unsubstituted phenyl-1-methyl-2-(1H)-pyridones, intermediates thereof and pharmaceutically acceptable salts.

The compounds of this invention may be represented by the following structural formula:

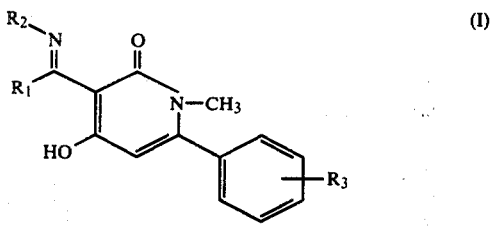

where $R_1$ represents straight chain lower alkyl, i.e., straight chain lower alkyl having 1 to 4 carbon atoms, e.g., methyl, ethyl, propyl and the like, or

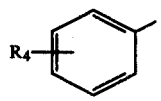

where
$R_4$ represents hydrogen or halo having an atomic weight of about 19 to 36, and
$R_2$ represents lower alkyl, i.e., alkyl having 1 to 4 carbon atoms, e.g., methyl, ethyl, isopropyl and the like, and
$R_3$ represents hydrogen or halo as defined above.

The compounds of formula (I) are prepared according to the following reaction scheme:

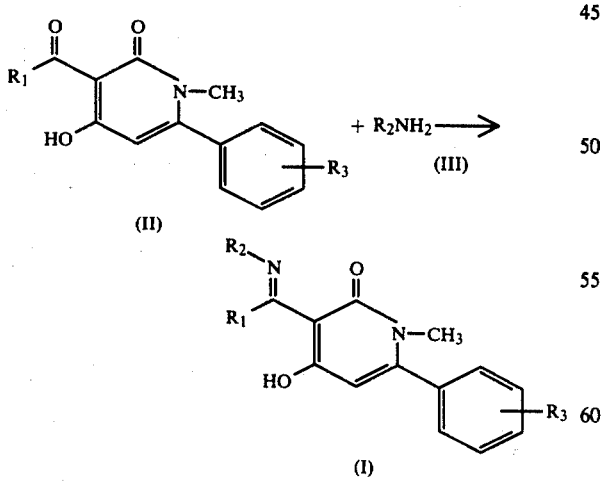

where $R_1$, $R_2$ and $R_3$ are as defined above.

The compounds of formula (I) are prepared by reacting a compound of the formula (II) with a compound of the formula (III) in the presence of an inert organic solvent. Although the particular solvent employed is not critical, the preferred solvents include the halogenated hydrocarbons such as methylene chloride, carbon tetrachloride, chloroform and the like, the aromatic hydrocarbons such as benzene, toluene and the like, or the lower alkanols such as ethanol, methanol and the like, preferably ethanol. The temperature of the reaction is not critical, but it is preferred that the reaction be run from about 25° to 105° C., preferably the reflux temperature of the solvent. The reaction is run from about 1 to 24 hours, preferably from about 2 to 5 hours. The product is recovered using conventional techniques, e.g., filtration.

The compounds of formula (II) are prepared according to the following reaction scheme:

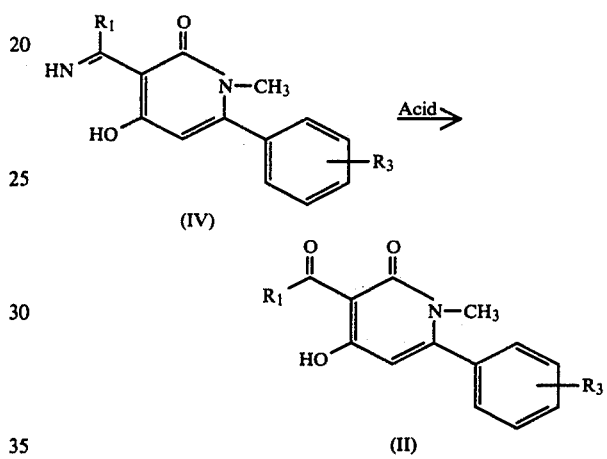

where $R_1$ and $R_3$ are as defined above.

The compounds of formula (II) are prepared by hydrolyzing a compound of the formula (IV) with an aqueous mineral acid such as sulfuric acid, phosphoric acid, or hydrochloric acid, the latter being especially preferred in the presence of an aqueous solvent. Although the preferred solvent is water, mixtures of water and water-miscible co-solvents such as tetrahydrofuran, dioxane, acetone or the lower alkanols such as methanol, ethanol and the like, can also be employed. The temperature of the reaction is not critical, but it is preferred that the reaction be run from about 25° to 105° C., preferably the reflux temperature of the solvent. The reaction is run from about 30 minutes to 24 hours, preferably from about 1 to 3 hours. The product is recovered using conventional techniques, e.g., trituration.

The compounds of formula (IV) are prepared according to the following reaction scheme:

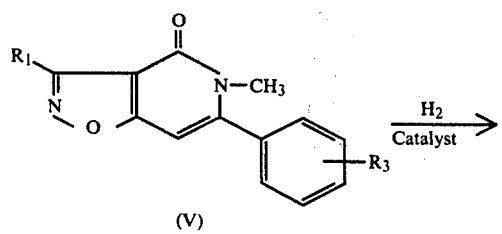

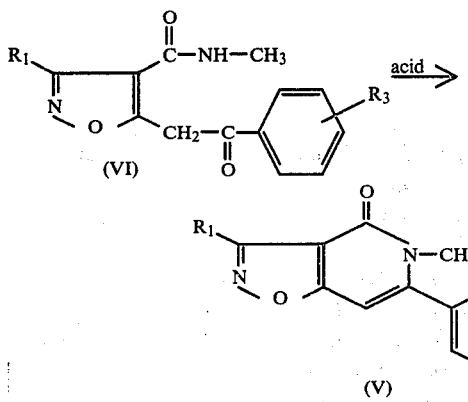

(VI)

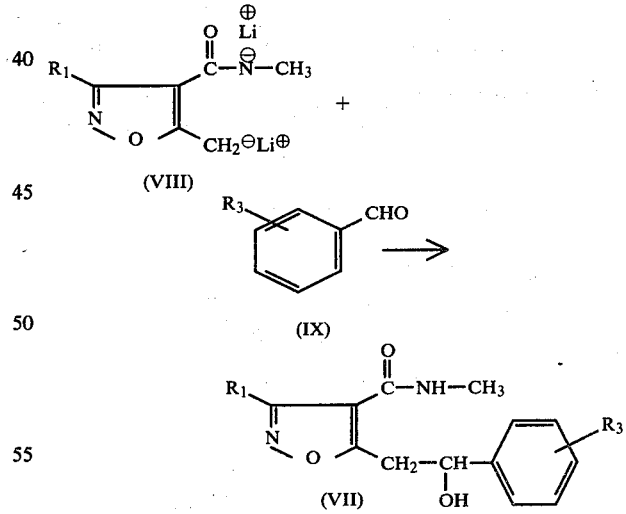

where $R_1$ and $R_3$ are as defined above.

The compounds of formula (V) are prepared by treating a compound of the formula (VI) with an acid, such as hydrochloric acid, p-toluenesulfonic acid, polyphosphoric acid or sulfuric acid, the latter being especially preferred, in the presence of an inert solvent. Although the particular solvent employed is not critical, the preferred solvents include the aromatic hydrocarbons, such as benzene, toluene and the like, or an excess of the acid utilized above, the latter being especially preferred. The temperature of the reaction is not critical, but it is preferred that the reaction be run from about 80° to 150° C., preferably the reflux temperature of the solvent. The reaction is run from about 12 to 36 hours, preferably from about 20 to 36 hours. The product is recovered using conventional techniques, e.g., trituration followed by recrystallization.

The compounds of formula (VI) are prepared in accordance with the following reaction scheme:

ered using conventional techniques, e.g., trituration followed by filtration.

The compounds of formula (VII) are prepared according to the following reaction scheme:

where $R_1$ and $R_3$ are as defined above.

The compounds of formula (VII) are prepared by treating a compound of the formula (VIII) with a compound of the formula (IX) in the presence of an inert organic solvent. Although the particular solvent employed is not critical, the preferred solvents include an ether such as diethylether or tetrahydrofuran or an aliphatic hydrocarbon such as pentene, hexane, heptane and the like, preferably tetrahydrofuran. The temperature of the reaction is not critical, but it is preferred that the reaction be run at a temperature of from about −75° to −55° C., preferably from about −65° to −60° C. The reaction is run from about 1 to 5 hours, preferably from about 2.5 to 3.5 hours. The product is recovered using conventional techniques, e.g., trituration followed by filtration.

The compounds of formula (VIII) are prepared according to the following reaction scheme:

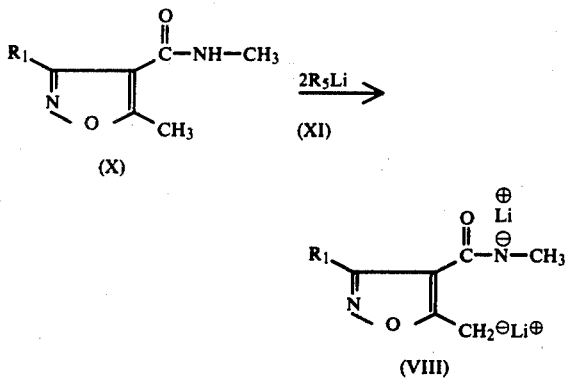

where

R$_5$ is lower alkyl having 1 to 4 carbon atoms, and
R$_1$ is as defined above.

The compounds of formula (VIII) are prepared by treating a compound of the formula (X) with a compound of the formula (XI) in the presence of an inert organic solvent. Although the particular solvent employed is not critical, the preferred solvents include an ether such as diethylether or tetrahydrofuran as an aliphatic hydrocarbon such as pentane, hexane, heptane and the like, preferably hexane. The temperature of the reaction is not critical, but it is preferred that the reaction be run at a temperature of from about −75° to −55° C., preferably from about −65° to −60° C. The reaction is run from about 1 to 5 hours, preferably from about 2.5 to 3.5 hours. The product of the compound of formula (X) is not isolated but employed in situ as a starting material in the preparation of the compounds of formula (VII).

Many of the compounds of formulae (III), (IX), (X), and (XI) are known and may be prepared by methods described in the literature. The compounds of formula (III), (IX), (X), and (XI) not specifically described may be prepared by analogous methods from known starting materials.

The compounds of formula (I) may also exist in the following tautomeric forms, and these tautomeric forms are also included within the scope of this invention.

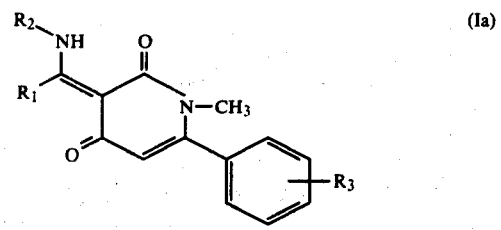

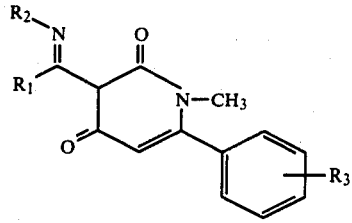

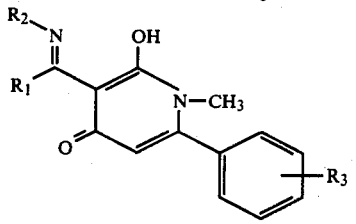

where
R$_1$, R$_2$ and R$_3$ are as defined above.

It is to be noted that the compounds of formula (I) also exist in the form of geometric isomers. In this regard, although only the cis form has been referred to in the case, the trans form is also contemplated within this invention.

The compounds of formula (I) are useful because they possess pharmacological activity in animals as sleep inducers, minor tranquilizers, muscle relaxants and neuroleptics as indicated (1) by the hexobarbital reinduction method of Winter, J. Pharmacol. and Exp. Therap., 94, 7–11, 1948, in which the reinduction of anethesia is used to determine sedativehypnotic activity in mice given 70 mg/kg of animal body weight i.p. of hexobarbital followed immediately after the mice regain their righting reflexes by 2 to 100 mg/kg of animal body weight i.p. of the test compound; (2) by their ability to produce docility in behavior tests in mice given 20 to 200 mg/kg of animal body weight, i.p. of the test compound according to the 30-word adjective check sheet system basically as described by Irwin S. (gordon Research Conference, Medicinal Chemistry, 1959) and Chen (Symposium on Sedative and Hypnotic Drugs, Williams and Wilkins, 1954); (3) by their ability to antagonize chlonic convulsions and death in mice given about 40.0 to 250 mg/kg of the test compound followed immediately by 50 mg/kg i.p. of N-sulfamoylazepine; (4) by scoring for loss of righting reflex according to the method of Reed-Muench (American Journal of Hygiene, 27: 493–497, 1938), in which mice are administered 12.5 mg/kg i.p. Thioridazine, immediately after which the test compound is administered at dosages of 20.0 to 100 mg/kg in a volume of 0.1 ml/10 g. body weight. Sixty minutes after dosing, the mice are scored for loss of righting reflex; (5) by the rotarod test as described by Dunham and Miya (J. Am. Pharm. Assoc., 45: 208, 1957); and (6) by the apomorphine gnawing test basically as described by the method of Ernst (Psychopharmacologica, 10: 316 to 323, 1967) in which male wistar rats weighing 90 to 110 g. are given 0.5 to 50.0 mg/kg p.o. of the test compound followed 30 minutes later by 10 mg/kg p.o. of apomorphine. It is well known that gnawing is induced by apomorphine and the test compound is said to have neuroleptic activity if it reduces gnawing activity in rats.

The sleep inducing effective dosage of the compounds of formula (I) will vary depending on the particular compound employed. However, in general, satisfactory results are obtained when the compounds are administered orally at a daily dosage of from about 1.0 milligram to about 200 milligrams per kilogram of animal body weight, typically given in a single dose at bedtime. For most large mammals, the total daily dosage is from about 20 to about 2000 milligrams, preferably at bedtime and dosage forms suitable for internal administration comprise from about 5.0 to about 1000 milligrams of the compound in admixture with a solid or liquid pharmaceutical carrier or diluent. The preferred pharmaceutical compositions from the standpoint of preparation and ease of administration are solid compositions, particularly hard-filled capsules and tablets.

For minor tranquilizer use in the treatment of anxiety and tension, the effective dosage will vary depending on the particular compound employed. However, in general, satisfactory results are obtained when the compounds are administered orally at a daily dosage of from about 10.0 milligram to about 500 milligrams per kilogram of animal body weight, typically given in divided doses two to four times per day. For most large mammals, the total daily dosage is from about 50 to about 2000 milligrams, and dosage forms suitable for internal administration comprise from about 12.5 to about 1000 milligrams of the compound in admixture with a solid or liquid pharmaceutical carrier or diluent.

For muscle relaxant use in the treatment of muscle spasms, the effective dosage will vary depending on the particular compound employed. However, in general, satisfactory results are obtained when the compounds are administered orally at a daily dosage of from about 10.0 milligram to about 500 milligrams per kilogram of animal body weight, typically given in divided doses two to four times per day. For most large mammals, the total daily dosage is from about 50 to about 2000 milligrams and dosage forms suitable for internal administration comprise from about 12.5 to about 1000 milligrams of the compound in admixture with a solid or liquid pharmaceutical carrier or diluent.

For neuroleptic use, the effective dose will vary depending on the particular compound employed and the severity of the condition being treated. However, in general, satisfactory results are obtained when the compounds are administered orally at a daily dosage of from about 1.0 milligrams to about 100 milligrams per kilogram of animal body weight, typically given in divided doses two to four times per day. For most large mammals, the total daily dosage is from about 1 to about 1000 milligrams and dosage forms suitable for internal administration comprise from about 0.25 to about 500 milligrams of the compound in admixture with a solid or liquid pharmaceutical carrier or diluent.

For the uses mentioned above, the compounds may be administered orally in such forms as tablets, capsules, elixirs, suspensions and the like or parenterally in the form of an injectable solutions or suspensions. The dosage will vary depending upon the mode of administration utilized and the compound employed.

The compounds of formula (I) may be similarly administered in the form of their non-toxic pharmaceutically acceptable salts. Such salts possess the same order of activity as the non-salt form and are readily prepared by reacting the molecule with an appropriate acid or an appropriate base by conventional technique and, accordingly, are included within the scope of this invention. Representative of such salts are the mineral acid salts, e.g., hydrochloride, hydrobromide, sulfate and the like, and the alkali metal salts such as sodium, potassium and the like.

Tablets and capsules containing the ingredients indicated below may be prepared by conventional techniques and are useful as sleep inducers at a dose of one or two tablets just before bedtime. Tablets and capsules containing the ingredients indicated below may also be useful as minor tranquilizers and muscle relaxants in divided doses two to four times per day.

| Ingredients | Weight (mg.) tablet | capsule |
| --- | --- | --- |
| 3-(α-N-methyliminobenzyl)-4-hydroxy-1-methyl-6-phenyl-2(1H)-pyridone | 200 | 200 |
| tragacanth | 10 | — |
| lactose | 247.5 | 300 |
| corn starch | 25 | — |
| talcum | 15 | — |
| magnesium stearate | 2.5 | — |
| TOTAL | 500 mg. | 500 mg. |

EXAMPLE 1

3-Phenyl-5-(β-hydroxyphenethyl)-N-methyl-isoxazole-4-carboxamide.

A suspension of 75 g. (0.348 mole) of 3-phenyl-5,N-dimethyl-isoxazole-4-carboxamide and 1 liter of tetrahydrofuran is cooled to −65° C. and 478 ml. of 1.6M n-butyllithium in hexane (0.765 mole) is added dropwise maintaining the temperature between −60° and −70° C. After the addition is complete, the orange suspension is stirred for 1½ hours at −60° to −70° C., and then 37.2 g. (0.350 mole) of benzaldehyde in 375 ml. tetrahydrofuran is added dropwise maintaining the temperature between −60° and −70° C. After addition is complete, the mixture is stirred 1½ hours at −60° to −70° C. and then warmed to −30° C. and quenched by the addition of saturated ammonium chloride solution. The mixture is further diluted with tetrahydrofuran and the layers are separated. The tetrahydrofuran layer is washed twice with 50% brine, and once with brine, dried over anhydrous magnesium sulfate, filtered and evaporated in vacuo. The solid residue is triturated with a 50:50 mixture of ether:petroleum ether, filtered and washed with cold ether to give 3-phenyl-5-(β-hydroxyphenethyl)-N-methyl-isoxazole-4-carboxamide, m.p. 183°–184° C.

Following the above procedure and using in place of 3-phenyl-5,N-dimethyl-isoxazole-4-carboxamide, an equivalent amount of (a) 3-(p-chlorophenyl)-5,N-dimethyl-isoxazole-4-carboxamide,
(b) 3-(p-fluorophenyl)-5,N-dimethyl-isoxazole-4-carboxamide, or
(c) 3-ethyl-5,N-dimethyl-isoxazole-4-carboxamide there is obtained
(a) 3-(p-chlorophenyl)-5-(β-hydroxyphenethyl)-N-methyl-isoxazole-4-carboxamide,
(b) 3-(p-fluorophenyl)-5-(β-hydroxyphenethyl)-N-methyl-isoxazole-4-carboxamide, or
(c) 3-ethyl-5-(β-hydroxyphenethyl)-N-methyl-isoxazole-4-carboxamide, respectively.

Again following the same procedure and using in place of benzaldehyde an equivalent amount of (d) p-chlorobenzaldehyde,
(e) p-fluorobenzaldehyde,
(f) m-fluorobenzaldehyde, or
(g) o-fluorobenzaldehyde there is obtained (d) 3-phenyl-5-(4-chloro-β-hydroxyphenethyl)-N-methyl-isoxazole-4-carboxamide,
(e) 3-phenyl-5-(4-fluoro-β-hydroxyphenethyl)-N-methyl-isoxazole-4-carboxamide,
(f) 3-phenyl-5-(3-fluoro-β-hydroxyphenethyl)-N-methyl-isoxazole-4-carboxamide, or
(g) 3-phenyl-5-(2-fluoro-β-hydroxyphenethyl)-N-methyl-isoxazole-4-carboxamide, respectively.

Furthermore, following the same procedure as outlined above and using in place of 3-phenyl-5,N-dimethyl-isoxazole-4-carboxamide an equivalent amount of 3-ethyl-5,N-dimethyl-isoxazole-4-carboxamide, and in place of benzaldehyde an equivalent amount of (d) p-chlorobenzaldehyde,
(e) p-fluorobenzaldehyde,
(f) m-fluorobenzaldehyde, or
(g) o-fluorobenzaldehyde there is obtained (h) 3-ethyl-5-(4-chloro-β-hydroxyphenethyl)-N-isoxazole-4-carboxamide,
(i) 3-ethyl-5-(4-fluoro-β-hydroxyphenethyl)-N-methyl-isoxazole-4-carboxamide,
(j) 3-ethyl-5-(3-fluoro-β-hydroxyphenethyl)-N-methyl-isoxazole-4-carboxamide, or
(k) 3-ethyl-5-(2-fluoro-β-hydroxyphenethyl)-N-methyl-isoxazole-4-carboxamide, respectively.

Also following the above procedure and using in place of 3-phenyl-5,N-dimethyl-isoxazole-4-carboxamide, an equivalent amount of 3-(p-fluorophenyl)-5,N-dimethyl-isoxazole-4-carboxamide, and in place of benzaldehyde an equivalent amount of p-fluorobenzaldehyde, there is obtained (l) 3-(p-fluorophenyl)-5-(4-fluoro-β-hydroxyphenethyl)-N-methyl-isoxazole-4-carboxamide.

EXAMPLE 2

N-methyl-5-phenacyl-3-phenyl-4-isoxazole carboxamide.

A suspension of 50 g. (0.155 mole) of 3-phenyl-5-(β-hydroxyphenethyl)-N-methyl-isoxazole-4-carboxamide and 800 ml. acetic acid at room temperature is treated dropwise rapidly with 18.4 g. (0.185 mole) of chromium trioxide in 185 ml. water. The resulting solution is stirred for 2 hours at room temperature and a portion of the acetic acid is removed in vacuo. The remainder is poured onto ice water and extracted with methylene chloride. The methylene chloride layer is washed with 2 N sodium hydroxide, dried over anhydrous magnesium sulfate, filtered and evaporated in vacuo. The solid residue is triturated with hot ether, cooled to 0° C. and filtered to give N-methyl-5-phenacyl-3-phenyl-4-isoxazole carboxamide, m.p. 125° to 128° C.

Following the above procedure and using in place of 3-phenyl-5-(β-hydroxyphenethyl)-N-methyl-isoxazole-4-carboxamide, an equivalent amount of (a) 3-(p-chlorophenyl)-5-(β-hydroxyphenethyl)-N-methyl-isoxazole-4-carboxamide,
(b) 3-(p-fluorophenyl)-5-(β-hydroxyphenethyl)-N-methyl-isoxazole-4-carboxamide,
(c) 3-ethyl-5-(β-hydroxyphenethyl)-N-methyl-isoxazole-4-carboxamide,
(d) 3-phenyl-5-(4-chloro-β-hydroxyphenethyl)-N-methyl-isoxazole-4-carboxamide,
(e) 3-phenyl-5-(4-fluoro-β-hydroxyphenethyl)-N-methyl-isoxazole-4-carboxamide,
(f) 3-phenyl-5-(3-fluoro-β-hydroxyphenethyl)-N-methyl-isoxazole-4-carboxamide,
(g) 3-phenyl-5-(2-fluoro-β-hydroxyphenethyl)-N-methyl-isoxazole-4-carboxamide,
(h) 3-ethyl-5-(4-chloro-β-hydroxyphenethyl)-N-methyl-isoxazole-4-carboxamide,
(i) 3-ethyl-5-(4-fluoro-β-hydroxyphenethyl)-N-methyl-isoxazole-4-carboxamide,
(j) 3-ethyl-5-(3-fluoro-β-hydroxyphenethyl)-N-methyl-isoxazole-4-carboxamide,
(k) 3-ethyl-5-(2-fluoro-β-hydroxyphenethyl)-N-methyl-isoxazole-4-carboxamide, or
(l) 3-(p-fluorophenyl)-5-(4-fluoro-β-hydroxyphenethyl)-N-methyl-isoxazole-4-carboxamide, there is obtained (a) N-methyl-5-phenacyl-3-(p-chlorophenyl)-4-isoxazole carboxamide,
(b) N-methyl-5-phenacyl-3-(p-fluorophenyl)-4-isoxazole carboxamide,
(c) 3-ethyl-N-methyl-5-phenacyl-4-isoxazole carboxamide,
(d) N-methyl-5-(4-chlorophenacyl)-3-phenyl-4-isoxazole carboxamide,
(e) N-methyl-5-(4-fluorophenacyl)-3-phenyl-4-isoxazole carboxamide,
(f) N-methyl-5-(3-fluorophenacyl)-3-phenyl-4-isoxazole carboxamide,
(g) N-methyl-5-(2-fluorophenacyl)-3-phenyl-4-isoxazole carboxamide,
(h) 3-ethyl-N-methyl-5-(4-chlorophenacyl)-4-isoxazole carboxamide,
(i) 3-ethyl-N-methyl-5-(4-fluorophenacyl)-4-isoxazole carboxamide,
(j) 3-ethyl-N-methyl-5-(3-fluorophenacyl)-4-isoxazole carboxamide,
(k) 3-ethyl-N-methyl-5-(2-fluorophenacyl)-4-isoxazole carboxamide, or
(l) N-methyl-5-(4-fluorophenacyl)-3-(p-fluorophenyl)-4-isoxazole carboxamide, respectively.

EXAMPLE 3

5-Methyl-3,6-diphenyl-isoxazolo[4,5-c]pyridin-4(5H)-one.

A mixture of 26.1 g.(0.0815 mole) of N-methyl-5-phenacyl-3-phenyl-4-isoxazole carboxamide and 261 ml. of 2 M sulfuric acid is refluxed for 24 hours. The mixture is cooled and extracted with methylene chloride. The methylene chloride layer is washed with water and then brine, dried over anhydrous magnesium sulfate, filtered and evaporated in vacuo. The residue is triturated with ether and then recrystallized from ethanol to give 5-methyl-3,6-diphenyl-isoxazole[4,5-c]pyridin-4(5H)-one, m.p. 149°–151.5° C.

Following the above procedure and using in place of N-methyl-5-phenacyl-3-phenyl-4-isoxazole carboxamide, an equivalent amount of

- (f) N-methyl-3-(3-fluorophenacyl)-3-phenyl-4-isoxazole carboxamide,
- (g) N-methyl-5-(2-fluorophenacyl)-3-phenyl-4-isoxazole carboxamide,
- (h) 3-ethyl-N-methyl-5-(4-chlorophenacyl)-4-isoxazole carboxamide,
- (i) 3-ethyl-N-methyl-5-(4-fluorophenacyl)-4-isoxazole carboxamide,
- (j) 3-ethyl-N-methyl-5-(3-fluorophenacyl)-4-isoxazole carboxamide,
- (k) 3-ethyl-N-methyl-5-(2-fluorophenacyl)-4-isoxazole carboxamide, or
- (l) N-methyl-5-(4-fluorophenacyl)-3-(p-fluorophenyl)-4-isoxazole carboxamide there is obtained

- (a) 5-methyl-3-(p-chlorophenyl)-6-phenyl isoxazolo[4,5-c]pyridin-4(5H)-one,
- (b) 5-methyl-3-(p-fluorophenyl)-6-phenyl-isoxazolo[4,5-c]pyridin-4(5H)-one,
- (c) 3-ethyl-5-methyl-6-phenyl-isoxazolo[4,5-c]pyridin-4(5H)-one,
- (d) 5-methyl-3-phenyl-6-(p-chlorophenyl)-isoxazolo[4,5-c]pyridin-4(5H)-one,
- (e) 5-methyl-3-phenyl-6-(p-fluorophenyl)-isoxazolo[4,5-c]pyridin-4(5H)-one,
- (f) 5-methyl-3-phenyl-6-(m-fluorophenyl)-isoxazolo[4,5-c]pyridin-4(5H)-one,
- (g) 5-methyl-3-phenyl-6-(o-fluorophenyl)-isoxazolo[4,5-c]pyridin-4(5H)-one,
- (h) 3-ethyl-5-methyl-6-(p-chlorophenyl)-isoxazolo[4,5-c]pyridin-4(5H)-one,
- (i) 3-ethyl-5-methyl-6-(p-fluorophenyl)-isoxazolo[4,5-c]pyridin-4(5H)-one,
- (j) 3-ethyl-5-methyl-6-(m-fluorophenyl)-isoxazolo[4,5-c]pyridin-4(5H)-one,
- (k) 3-ethyl-5-methyl-6-(o-fluorophenyl)-isoxazolo[4,5-c]pyridin-4(5H)-one, or
- (l) 5-methyl-3-(p-fluorophenyl)-6-(p-fluorophenyl)isoxazolo[4,5-c]pyridin-4(5H)-one, respectively.

EXAMPLE 4

3-($\alpha$-iminobenzyl)-4-hydroxy-6-phenyl-1-methyl-2(1H)-pyridone.

A mixture of 16.5 g. (0.0545 mole) of N-methyl-3,6-diphenyl-isoxazolo[4,5-c]pyridin-4(5H)-one, 330 ml. ethanol and 1.65 g. 10% palladium on carbon is hydrogenated at 50 psi and room temperature. The hydrogenation is ceased after 1 equivalent of hydrogen is absorbed (ca 2.5 hours). The mixture is treated with methylene chloride and the catalyst is removed by filtration. The solvents are removed in vacuo to a volume of ca. 50 ml. and then ether is added, to precipitate solids which are removed by filtration to give 3-($\alpha$-iminobenzyl)-4-hydroxy-6-phenyl-1-methyl-2(1H)-pyridone, m.p. 238°–240° C. The above compound is dissolved in meth-

- (b) 3-ethyl-5-methyl-6-phenyl-isoxazolo[4,5-c]pyridin-4(5H)-one,
- (c) 3-ethyl-5-methyl-6-phenyl-isoxazolo[4,5-c]pyridin-4(5H)-one,
- (d) 5-methyl-3-phenyl-6-(p-chlorophenyl)-isoxazolo[4,5-c]pyridin-4(5H)-one,
- (e) 5-methyl-3-phenyl-6-(p-fluorophenyl)-isoxazolo[4,5-c]pyridin-4(5H)-one,
- (f) 5-methyl-4-phenyl-6-(m-fluorophenyl)-isoxazolo[4,5-c]pyridin-4(5H)-one,
- (g) 5-methyl-3-phenyl-6-(o-fluorophenyl)-isoxazolo[4,5-c]pyridin-4(5H)-one,
- (h) 3-ethyl-5-methyl-6-(p-chlorophenyl)-isoxazolo[4,5-c]pyridin-4(5H)-one,
- (i) 3-ethyl-5-methyl-6-(p-fluorophenyl)-isoxazolo[4,5-c]pyridin-4(5H)-one,
- (j) 3-ethyl-5-methyl-6-(m-fluorophenyl)-isoxazolo[4,5-c]pyridin-4(5H)-one,
- (k) 3-ethyl-5-methyl-6-(o-fluorophenyl)-isoxazolo[4,5-c]pyridin-4(5H)-one, or
- (l) 5-methyl-3-(p-fluorophenyl)-6-(p-fluorophenyl)-isoxazolo[4,5-c]pyridin-4(5H)-one there is obtained

- (a) 3-($\alpha$-imino-p-chlorobenzyl)-4-hydroxy-6-phenyl-1-methyl-2(1H)-pyridone,
- (b) 3-($\alpha$-imino-p-fluorobenzyl)-4-hydroxy-6-phenyl-1-methyl-2(1H)-pyridone,
- (c) 3-(1-iminopropyl)-4-hydroxy-6-phenyl-1-methyl-2(1H)-pyridone,
- (d) 3-($\alpha$-iminobenzyl)-4-hydroxy-6-(p-chlorophenyl)-1-methyl-2(1H)-pyridone,
- (e) 3-($\alpha$-iminobenzyl)-4-hydroxy-6-(p-fluorophenyl)-1-methyl-2(1H)-pyridone,
- (f) 3-($\alpha$-iminobenzyl)-4-hydroxy-6-(m-fluorophenyl)-1-methyl-2(1H)-pyridone,
- (g) 3-($\alpha$-iminobenzyl)-4-hydroxy-6-(o-fluorophenyl)-1-methyl-2(1H)-pyridone,
- (h) 3-(1-iminopropyl)-4-hydroxy-6-(p-chlorophenyl)-1-methyl-2(1H)-pyridone,
- (i) 3-(1-iminopropyl)-4-hydroxy-6-(p-fluorophenyl)-1-methyl-2(1H)-pyridone,
- (j) 3-(1-iminopropyl)-4-hydroxy-6-(m-fluorophenyl)-1-methyl-2(1H)-pyridone,
- (k) 3-(1-iminopropyl)-4-hydroxy-6-(o-fluorophenyl)-1-methyl-2(1H)-pyridone, or
- (l) 3-($\alpha$-imino-p-fluorobenzyl-4-hydroxy-6-(p-fluorophenyl)-1-methyl-2(1H)-pyridone, respectively.

EXAMPLE 5

3-benzoyl-4-hydroxy-6-phenyl-1-methyl-2(1H)-pyridine.

A mixture of 5 grams (0.0164 mole) of 3-($\alpha$imino-benzyl)-4-hydroxy-6-phenyl-1-methyl-2(1H)-pyridone and 50 ml. 6 N hydrochloric acid is refluxed for 1.5 hours. The resulting mixture is then cooled and extracted with

United States Patent [19]

Nielsen

[11] 4,170,706

[45] Oct. 9, 1979

[54] METHOD FOR PREPARING THE BISPICRATE SALT OF 2,3,7,8-TETRAAZASPIRO[4.4]NONANE

[75] Inventor: Arnold T. Nielsen, China Lake, Calif.

[73] Assignee: The United States of America as represented by the Secretary of the Navy, Washington, D.C.

[21] Appl. No.: 937,635

[22] Filed: Aug. 28, 1978

Related U.S. Application Data

[62] Division of Ser. No. 829,761, Sep. 1, 1977, Pat. No. 4,125,728, which is a division of Ser. No. 743,723, Nov. 22, 1976, Pat. No. 4,066,833.

[51] Int. Cl.² .......................................... C07D 487/10
[52] U.S. Cl. .................................................. 548/356
[58] Field of Search ........................ 548/356; 568/710

[56] References Cited

PUBLICATIONS

Auwers et al., Chem. Ber. 1936, vol. 69, pp. 2347–2351.
Wertheim, Textbook of Organic Chemistry, Blakiston, N.Y., 1951, p. 568.

*Primary Examiner*—Alan L. Rotman
*Assistant Examiner*—Natalia Harkaway
*Attorney, Agent, or Firm*—R. S. Sciascia; W. Thom Skeer; L. E. K. Pohl

[57] ABSTRACT

Synthetic routes to 2,3,7,8-tetraazaspiro[4.4]nonane, its bispicrate salt, 2,3,7,8-tetraazaspiro[4.4]nona-2,7-diene, and 3,8-dicarbomethoxy-2,3,7,8-tetraazaspiro[4.4]nona-1,6-diene. The compounds are useful as high density fuels.

2 Claims, No Drawings